United States Patent
Tilmans et al.

(10) Patent No.: US 8,283,923 B2
(45) Date of Patent: Oct. 9, 2012

(54) MECHANICAL PICK-UP WITH REDUCED IMPACT FORCE BY USING A ROTATING INTERMEDIATE PART

(75) Inventors: Hubertus Antonius Tilmans, Best (NL); Adrianus Johannes Josephus van der Horst, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 377 days.

(21) Appl. No.: 12/680,217

(22) PCT Filed: Sep. 24, 2008

(86) PCT No.: PCT/IB2008/053876
§ 371 (c)(1),
(2), (4) Date: Mar. 26, 2010

(87) PCT Pub. No.: WO2009/040741
PCT Pub. Date: Apr. 2, 2009

(65) Prior Publication Data
US 2010/0301863 A1    Dec. 2, 2010

(30) Foreign Application Priority Data
Sep. 28, 2007  (EP) .................................. 07117527

(51) Int. Cl.
*G01V 3/00* (2006.01)
(52) U.S. Cl. ...................................... 324/307; 324/309

(58) Field of Classification Search .......... 324/300–322; 600/407–445; 108/143, 5; 5/601, 943; 278/209; 378/209
See application file for complete search history.

(56) References Cited

U.S. PATENT DOCUMENTS

| | | | |
|---|---|---|---|
| 4,475,072 A | 10/1984 | Schwehr et al. | |
| 4,926,455 A | 5/1990 | Stojkov et al. | |
| 5,010,564 A | 4/1991 | Thomas | |
| 5,210,893 A | 5/1993 | Uosaki et al. | |
| 5,273,043 A * | 12/1993 | Ruike | 600/436 |
| 6,499,159 B1 * | 12/2002 | Schmitt et al. | 5/601 |
| 6,615,428 B1 | 9/2003 | Pattee | |
| 6,637,056 B1 * | 10/2003 | Tybinkowski et al. | 5/611 |
| 6,955,464 B1 | 10/2005 | Tybinkowski et al. | |
| 2007/0086577 A1 | 4/2007 | Kobayashi | |

FOREIGN PATENT DOCUMENTS

| | | |
|---|---|---|
| EP | 0857458 A1 | 8/1998 |
| WO | 2004047639 A1 | 6/2004 |

* cited by examiner

*Primary Examiner* — Brij Shrivastav

(57) ABSTRACT

When a subject is being positioned in a diagnostic imager for a diagnostic scan, a subject support (26) often picks up an accessory carriage (24) along the way without stopping or reducing velocity. To reduce stresses on the subject support (26), accessory carriage (24) and on the subject themselves, an apparatus and method are provided for gradually accelerating the accessory carriage (26) to the speed of the subject support (26). A camming surface (60) engages a pin (54*b*) of a snap block (52) causing translational motion to be converted into rotational motion, spreading the acceleration of the accessory carriage (24) over a distance $(d-d_1)$.

15 Claims, 4 Drawing Sheets

MECHANICAL PICK-UP WITH REDUCED IMPACT FORCE BY USING A ROTATING INTERMEDIATE PART

The following relates to the diagnostic imaging arts. It finds particular application in connection with loading and unloading an accessory device into and out of an imaging region of a magnetic resonance imaging device along with a subject support and will be described with particular reference thereto. It is to be understood that the present application is also applicable to other situations where one movable system needs to be smoothly accelerated to the speed of another movable system, and is not limited to the above referenced application.

In a magnetic resonance imaging environment, it is often advantageous to use local dedicated receive coils in conjunction with the full body RF coils to receive magnetic resonance signals. Often, such local coils are embodied in separate accessory carriages that move along with the subject support. Another example may be an X-ray film cartridge that moves along with the subject support as the subject is being positioned for an optimal X-ray image. As the accessory devices are not always used, or sometimes it is advantageous to remove the accessory carriage, they are not permanently affixed to the subject support.

When the subject is ready to be imaged, the subject support starts to move, and on its way into the imaging region, the accessory carriage also moves along with it. On arrival at the correct location, the accessory carriage is released from the subject support and locked by the stationary component. Several problems arise when releasing the accessory carriage in this manner. The accessory carriage is not negligible in weight, and can significantly disrupt the movement of the subject support during release. This abrupt velocity change of the accessory carriage can be noisy and uncomfortable to the subject, as the subject is located close above the release point. The subject support can be jolted as the subject support releases the accessory carriage, leading to further discomfort of the subject, who is likely already apprehensive about undergoing an imaging scan. Apart from concerns of the subject, an abrupt velocity change can damage the device carried on the accessory carriage. For example, printed circuit boards that may be part of coil electronics can be damaged or broken. After completing the scan the subject support returns to its starting position and the accessory carriage is picked up again.

Mechanical dampeners, such as springs have been used to ease the transition during release and pickup of the accessory carriage. Hysteresis problems can be associated with mechanical dampeners. Additionally, if the spring does not return to its original compression, problems with positioning the accessory carriage relative to the subject support can arise. Also, the problems with noise and subject jolting are not totally eliminated.

The following provides new and improved devices and methods which overcome the above-referenced problems and others.

In accordance with one aspect, a diagnostic imaging device is provided. A gantry defines an imaging region. An accessory device carriage houses an accessory device for selective use in the imaging region during a diagnostic imaging scan. The carriage includes a rotatable snap block. A subject support supports a subject and moves the subject into and out of the imaging region. The subject support includes a first carriage pickup element for engaging the rotatable snap block of the accessory device carriage and gradually accelerates or decelerates the accessory device carriage to the speed of the subject support.

In accordance with another aspect, a diagnostic imaging apparatus is provided. A gantry defines an imaging region. An accessory device carriage houses an accessory device for selective use in the imaging region during a diagnostic imaging scan. The carriage includes a fixed snap block. A subject support supports a subject and moves the subject into and out of the imaging region. The subject support includes a first rotatable carriage pickup element for engaging the fixed snap block of the accessory device carriage and gradually accelerating the accessory device carriage to the speed of the subject support.

In accordance with another aspect, a magnetic resonance imaging scanner is provided. A gantry houses a main magnetic coil that generates a substantially uniform main magnetic field in an imaging region of the gantry. A subject support positions a subject within the imaging region. A gradient coil assembly superimposes gradient fields on the main magnetic field. An RF coil assembly transmits RF signals into the imaging region, and detects magnetic resonance signals from the imaging region. A local RF receive coil is carried by an accessory carriage. The accessory carriage has a rotatable snap block for engaging at least one carriage pickup device on the subject support. The rotatable snap block accelerates the accessory carriage to the speed of the subject support when the snap block engages at least one carriage pickup device.

In accordance with another aspect, a method of diagnostic imaging is provided. A subject support is translated into an imaging region of a diagnostic imaging device. An accessory carriage is accelerated to a velocity of the subject support by engaging a snap block attached to the accessory carriage with a first carriage pickup element attached to the subject support. After the first carriage pickup element engages the snap block, translational motion of the first subject support is converted into rotational motion.

One advantage lies in reduced stress on sensitive accessory carriage components.

Another advantage lies in quieter uptake of the accessory carriage.

Another advantage lies in reduced stress on the subject.

Still further advantages will be appreciated by those of ordinary skill in the art upon reading and understand the following detailed description.

The invention may take form in various components and arrangements of components, and in various operations and arrangements of operations. The drawings are only for purposes of illustrating the preferred embodiments and are not to be construed as limiting the invention.

Figure 1:
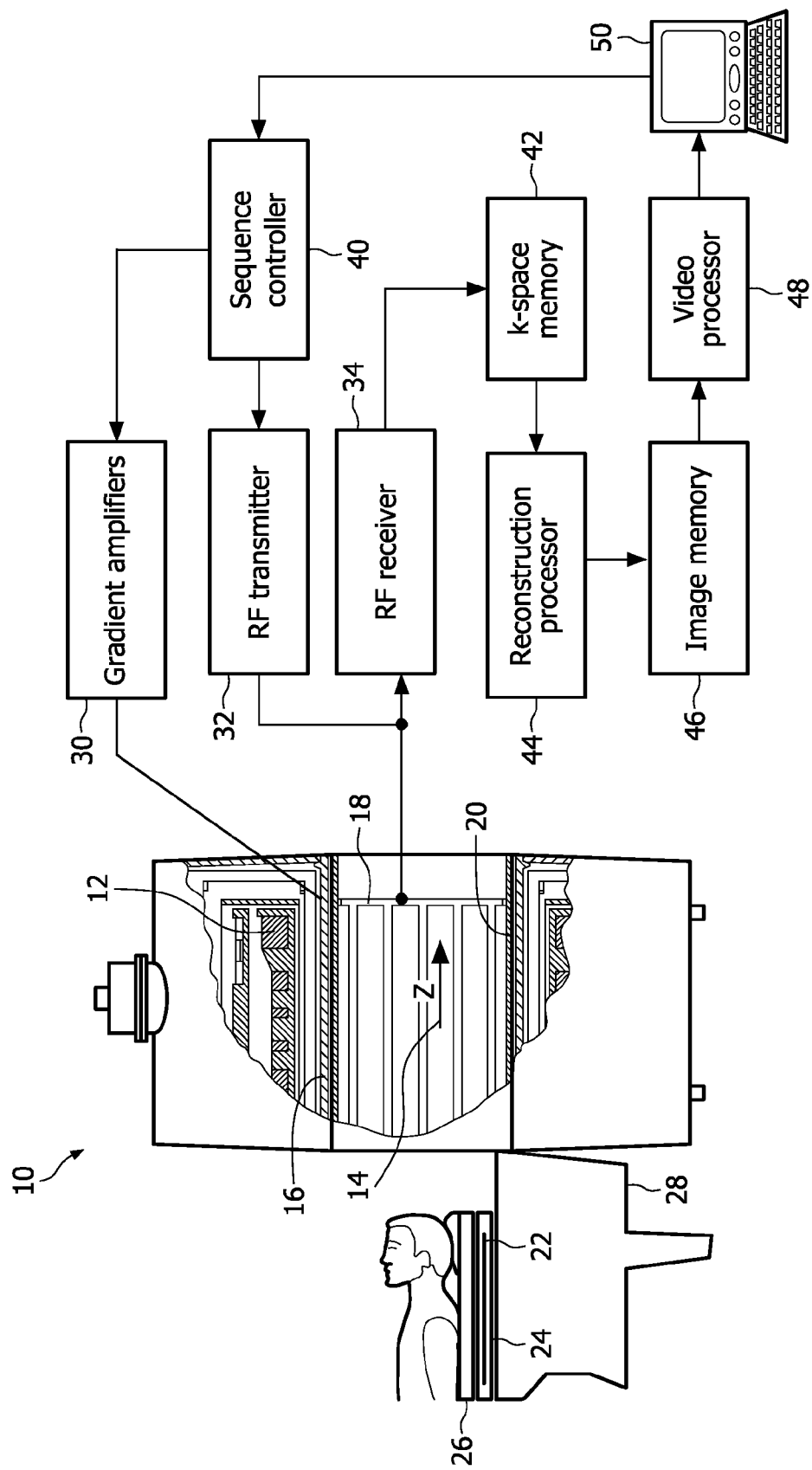
FIG. 1 is a diagrammatic illustration of a magnetic resonance system.

With reference to FIG. 1, a magnetic resonance scanner 10 includes a cylindrical main magnet assembly 12. The illustrated main magnet assembly 12 includes a superconducting cryoshielded solenoid defining a bore 14 into which a subject is placed for imaging. The main magnet assembly 12 produces a substantially constant main magnetic field oriented along a longitudinal (z) axis of the bore 14. Although a cylindrical main magnet assembly 12 is illustrated, it is to be understood that other magnet arrangements, such as vertical field, open magnets, non-superconducting magnets, and other configurations are also contemplated. Additionally, other diagnostic imaging systems could be used, such as CT, PET, SPECT, x-ray, ultrasound, and others.

A gradient coil 16 produces magnetic field gradients in the bore 14 for spatially encoding magnetic resonance signals, for producing magnetization-spoiling field gradients, or the like. In some embodiments, the magnetic field gradient coil 16 includes coil segments configured to produce magnetic field gradients in three orthogonal directions, such as longitudinal or z, transverse or x, and vertical or y directions.

An optional whole body radio frequency coil assembly 18 generates radio frequency pulses for exciting magnetic resonance in dipoles of the subject. Alternatively, a local coil or coil array can be used to excite the magnetic resonance. Optionally, the whole body radio frequency coil assembly 18 also serves to detect magnetic resonance signals emanating from the imaging region. Alternatively, a local coil or coil array can be used for this purpose. In FIG. 1, a radio frequency shield 20 is placed between the RF coils 18 and the gradient coils 16.

An additional accessory device 22, such as a local coil array 22, is located within an accessory carriage 24 for more sensitive, localized spatial encoding, excitation, and reception of magnetic resonance signals. Various types of local coil arrays are contemplated such as a surface RF coil with one radio frequency coupling, a quadrature coil assembly with two radio frequency couplings, a phased array with several couplings, a SENSE coil array with a plurality of radio frequency couplings, combined RF and gradient coils, and the like. In some applications, the accessory device 22 is a spine coil. More generally, the accessory device 22 can be any device that is suitably located beneath the subject for a given application, such as an X-ray film cartridge in the case of an x-ray fluoroscope, or the like. The subject is disposed upon a subject support 26, such as a tabletop, positioned above the accessory carriage 24. The tabletop 26 and accessory carriage 24 are initially positioned on a couch, trolley, or other patient preparation stage 28, with the subject support tabletop 26 arranged to slide into and then out of the bore of the magnetic resonance scanner 10 to effectuate subject loading and unloading.

In the illustrated example of a magnetic resonance system, gradient pulse amplifiers 30 deliver controlled electrical currents to the magnetic field gradient coils 16 to produce selected magnetic field gradients. The gradient amplifiers also deliver electrical pulses to the gradient coils of local coil arrays that are equipped with gradient coils. A radio frequency transmitter 32, preferably digital, applies radio frequency pulses or pulse packets to the radio frequency coil assembly 18 or to another excitation coil or coil array to generate selected magnetic resonance excitation. A radio frequency receiver 34 is coupled to the local coil 22 or to another receive coil or coil array to receive and demodulate the induced magnetic resonance signals.

To acquire magnetic resonance imaging data of a subject, the subject is placed inside the magnet bore 14, with the imaged region at or near an isocenter of the main magnetic field. A sequence controller 40 communicates with the gradient amplifiers 30 and the radio frequency transmitter 32 to produce selected transient or steady-state magnetic resonance sequences, to spatially encode such magnetic resonances, to selectively spoil magnetic resonances, or otherwise generate selected magnetic resonance signals characteristic of the subject. The generated magnetic resonance signals are detected by the local coil 22 and the full body coil 18, communicated to the radio frequency receiver 34, and stored in a k space memory 42. The imaging data is reconstructed by a reconstruction processor 44 to produce an image representation that is stored in an image memory 46. In one suitable embodiment, the reconstruction processor 44 performs an inverse Fourier transform reconstruction.

The resultant image representation is processed by a video processor 48 and displayed on a user interface 50 equipped with a human readable display. The interface 50 is preferably a personal computer or workstation. Rather than producing a video image, the image representation can be processed by a printer driver and printed, transmitted over a computer network or the Internet, or the like. In the embodiment shown in FIG. 1, the user interface 50 also allows a radiologist or other operator to communicate with the magnetic resonance sequence controller 40 to select magnetic resonance imaging sequences, modify imaging sequences, execute imaging sequences, and so forth.

Not every imaging scan calls for the use of the local coil 22, rather that determination is made on a scan by scan basis. Some sequences, such as spinal imaging sequences, suitably employ the local coil 22 underneath the subject, while other sequences may not call for use of the local coil 22. If the local coil 22 is to be used, then the accessory carriage 24 is disposed beneath the subject support 26. In some embodiments, the carriage 24 engages a barrier or a latch so that the user is made aware that the carriage 24 is aligned to be picked up by the subject support 26.

The accessory carriage 24 is attached to the subject support 26 and is moved into the scanner bore and released at the correct location using a mechanical pickup/release mechanism that employs at least one rotatable element configured to cam against pre-defined curved surfaces to gradually decelerate the coil carriage 24 from the tabletop speed to standstill. Various configurations of rotatable elements can be used, and the curvature or shape of the camming surface or surfaces can be selected to impart a selected gradual acceleration to the accessory carriage. Moreover, the same mechanism is used to accelerate the accessory carriage 24 and attach it to the subject support 26. Together, the subject support 26 and the accessory carriage 24 approach their rest position over the couch or trolley 28 outside of the scanner 10. A set of rollers, ball bearings, or so forth can also be substituted for the camming mechanism.

Figure 2:
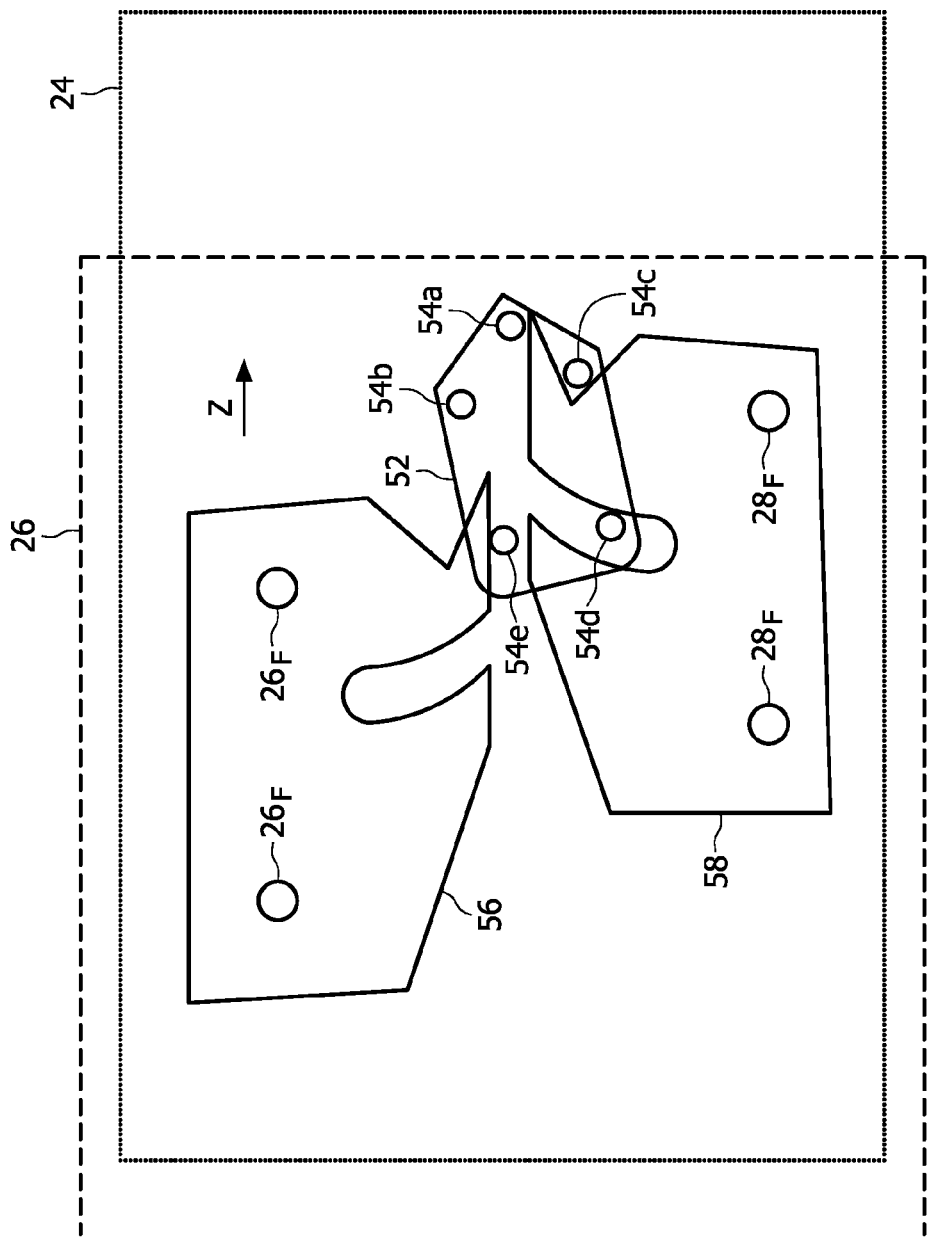
FIG. 2 illustrates an orientation of a pickup device of the system of FIG. 1 before a first carriage engagement element has engaged a snap block.

With reference now to FIG. 2, an illustrative pickup for the accessory carriage 24 is described as an example. A rotating element such as an illustrated snap block 52 is mounted to the accessory carriage 24. In the illustrated embodiment, the snap block is operatively connected with five pins 54a-e that engage various surrounding surfaces. The snap block 54 is rotatably mounted to the accessory carriage 24 and by a head pin 54a. A first carriage pickup element 56 is fixedly mounted to the subject support 26 and translates therewith along the longitudinal (z) axis of the bore 14. A second carriage pickup device 58 is secured to the couch or trolley 28 and serves as an anchor or starting point for the snap block 52, as depicted in FIG. 2. In the illustrated embodiment, the fixed element 56 is secured to the subject support, e.g. tabletop 26, by fasteners 26$_F$ while the fixed element 58 is secured to the couch or trolley by fasteners 28$_F$. Alternatively, the fixed elements 56, 58 may be integrally formed with the tabletop 26 and/or couch or trolley 28.

Figure 3:
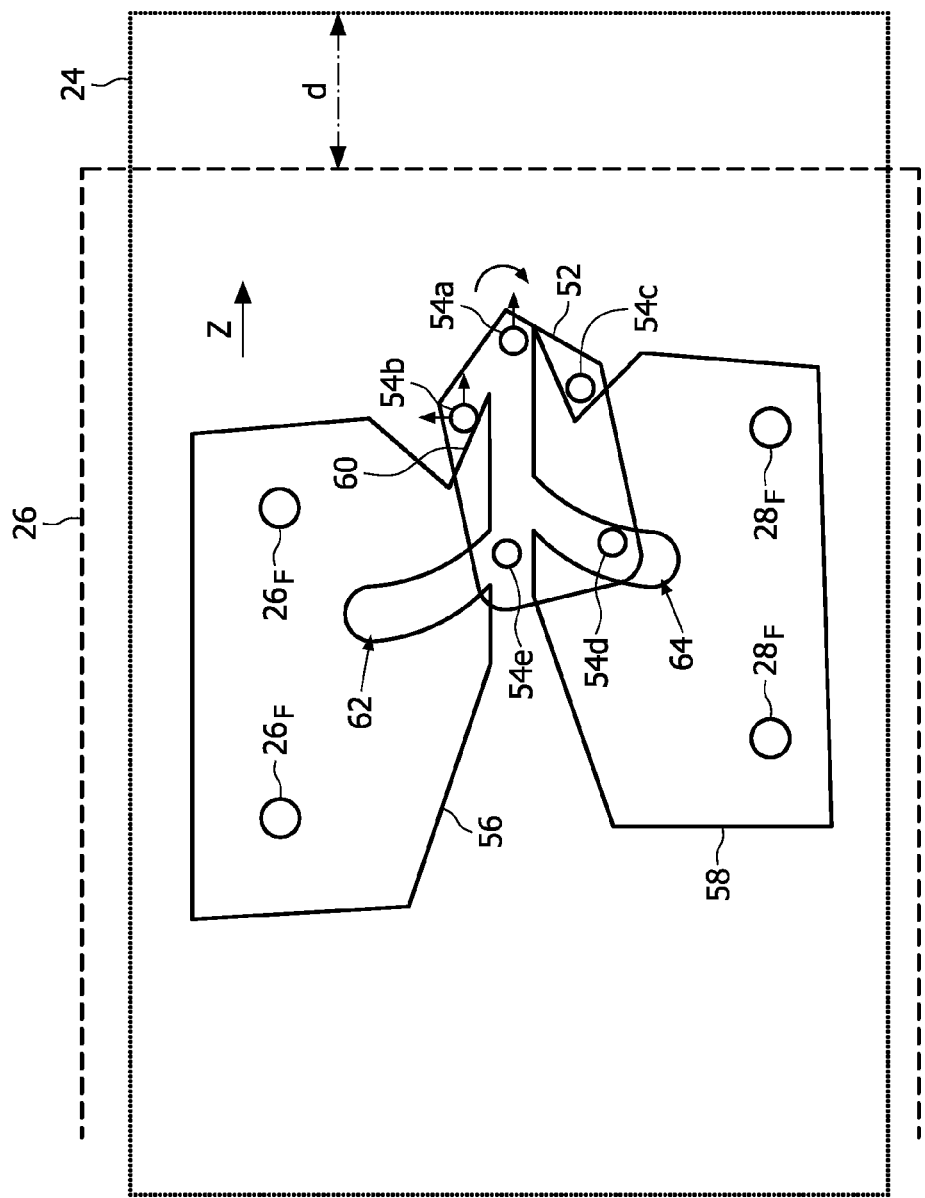
FIG. 3 illustrates the position of the elements of the pickup device as the first carriage element engages the snap block.

During unloading, the subject support 26 moves in the direction indicated in FIG. 2. Once the first carriage pickup element 56 secured to the subject support 26 moves far enough, a first camming surface 60 engages pin 54b of the snap block 52, as shown in FIG. 3. As the first carriage pickup element 56 continues parallel to the longitudinal (z) axis of the bore 14, the first camming surface 60 urges the pin 54b forward in the same direction, but since the snap block 52 is rotatable about the pin 54a, the first camming surface 60 also urges the pin 54b upwards, as indicated by the arrows in FIG. 3. Consequently, the pin 54e enters a take-over groove 62 in the first carriage pickup element 56. Similarly, the pin 54d begins to exit a take-over groove 64 in the second carriage pickup element 58. The forward component of the pin 54b is matched by the pin 54a and hence, the snap block 52 and the accessory carriage 24. At the start of motion of the snap block, a distance d exists between the leading edge of the subject support 26 and the leading edge of the accessory carriage 24.

Figure 4:
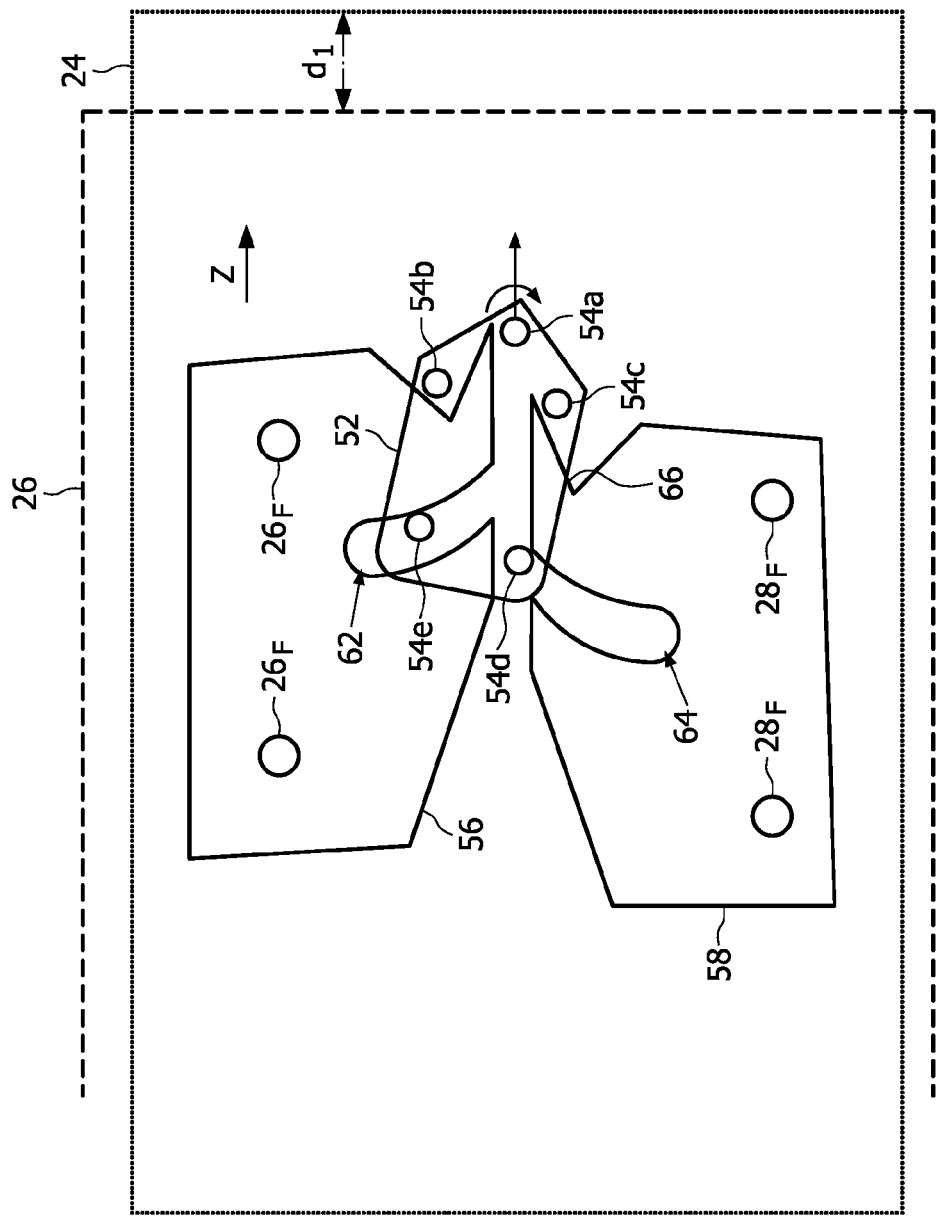
FIG. 4 illustrate an orientation of the elements of the pickup device after an accessory carriage has been accelerated to the speed of the subject support.

As the first carriage pickup element 56 proceeds on with constant velocity, the snap block 52 (and hence the accessory carriage 24 attached at pin 54a) is gradually accelerated in the same direction. With reference now to FIG. 4, the pin 54e proceeds up the take-over groove 62 until it cannot move anymore. Also pin 54d moves out of groove 64 and helps the snap block 52 to rotate. When pin 54d is completely out of the groove 64 the snap block 52 stops its rotational motion. Since the translational motion is no longer being converted into rotational motion, the snap block 52 (and the accessory carriage 24 attached thereto) matches the forward speed of the first carriage pickup element 56 and the subject support 26. In this position, with the snap block 52 no longer rotating, the distance d has diminished to a distance $d_1$. The translational motion of the first carriage pickup element 56 is partially converted into rotational motion by the snap block 52. As a result, the acceleration of the accessory carriage is spread over a difference of the distances d and $d_1$. Thus, the impact of the accessory carriage 24 pickup is gradual rather than abrupt.

In one embodiment, the snap block 52, first carriage pickup element 56 and second carriage pickup element 58 remain outside of the imaging region of the device 10 while a scan is being performed. An optical encoding device can be used to determine the position of the subject support 26. Since the pickup mechanism does not employ elastic components such as a spring, there is no hysteresis or other source of positional uncertainty and so the position of the accessory carriage 24 can be accurately inferred from the position of the subject support 26. A latching device (not shown) can be employed to ensure that the subject support 26 remains stationary during the imaging scan.

During load, the process is performed in reverse. In the illustrated example, the stationary components 56, 58 are mirror images of each other, and the snap block 52 has bilateral symmetry, so that the carriage release process as the withdrawing tabletop 26 and carried accessory carriage 24 approach the rest position on the couch or trolley 28 is analogous to the release process. Starting with FIG. 4, the subject support 26 and the accessory carriage 24 start moving in the opposite direction from the direction they were moving before the scan. When the pin 54c contacts a second camming surface 66, the second camming surface 66 urges the pin 54c down. This starts rotating the snap block 52 in the opposite direction, and the pin 54e begins to exit the take-over groove 62 and the pin 54d begins to enter the take-over groove 64. Once again, the translational motion of the accessory carriage 24 is converted into rotational motion of the snap block 52, slowing down the accessory carriage 24 while the subject support 26 keeps moving with constant speed. Once the pin 54d cannot move anymore, that is, once the system has returned to the configuration of FIG. 3, the snap block 52 stops rotating, and the accessory carriage 24 matches the speed of the second carriage pickup element 58, which is fixed in space, i.e. zero. Again, instead of coming to a stop with a jolt over virtually no distance, the accessory carriage is decelerated over the distance $d-d_1$.

In some alternate embodiments, the snap block 52 is contemplated to be fixedly attached to the accessory carriage 24 instead of rotatably attached. In these embodiments, the first and second carriage pickup elements 56, 58 are rotatably attached. Like the previous embodiment, translational motion is converted into rotational motion, but instead of the snap block 52 rotating, the first and second carriage pickup elements 56, 58 rotate. Other configurations of camming, sliding, ball bearing or roller-mediated coupling, or so forth are also contemplated to effectuate conversion of the forward motion of the subject support 24 into rotational motion, so as to gradually accelerate the accessory carriage over a distance instead of abruptly catching the accessory carriage.

In some embodiments, the camming surfaces have curvature designed to provide substantially constant one-gravity acceleration from stationary up to the tabletop speed. Accelerations faster or slower than one-gravity are also contemplated. Moreover, the camming surfaces can be designed to provide a non-constant acceleration from stationary up to the tabletop speed. In general, one can readily design the camming surface curvatures to provide any desired acceleration profile.

The acceleration profile is related to the horizontal and vertical positions of the pins, especially the pivot pin 54a that attaches the rotating element 52 to the accessory carriage 24. Depending upon the configuration of the subject support 26, the accessory carriage 24, and the couch or trolley 28, it may be possible for the weight of the subject on the subject support 26 to produce enough vertical (downward) displacement of the subject support 26 to vertically move the pivot pin 54a, which can then result in an error in the relative horizontal positions of the accessory carriage 24 and subject support 26. In such a case, the position of the accessory carriage 24 inferred from the position of the subject support 26 in the scanner bore would have some error. To accommodate vertical (downward) movement of the subject support 26, in some embodiments the pivot pin is mounted on an elongated member, such as a bar, and leaf springs or other elastic elements are used to isolate the pivot pin from any vertical motion of the subject support.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. An imaging device comprising:
    an imager defining an imaging region;
    an accessory device carriage that houses an accessory device for selective use in the imaging region, the carriage including a rotatable element;
    a subject support for supporting a subject and moving the subject into and out of the imaging region, the subject support including a first carriage pickup element for engaging the rotatable element of the accessory device carriage and gradually accelerating the accessory device carriage to the speed of the subject support.

2. The imaging device as set forth in claim 1, further including:
    a second carriage pickup element for engaging the rotatable element as the subject support exits the imaging region and gradually decelerating the accessory device carriage from the speed of the subject support to rest.

3. The imaging apparatus as set forth in claim 1, wherein the rotatable element converts translational motion into rotational motion as it accelerates and decelerates the accessory carriage device.

4. The imaging apparatus as set forth in claim 1, wherein the imager is a magnetic resonance scanner and the accessory device includes a radio frequency coil.

5. A method of diagnostic imaging comprising:
    translating a subject support into an imaging region of an imaging device; and
    accelerating an accessory carriage to a velocity of the subject support by engaging a snap block attached to the accessory carriage with a first carriage pickup element attached to the subject support such that as the first carriage pickup element engages the snap block, translational motion of the first subject support is converted into rotational motion.

6. The method as set forth in claim 5, further including:
    accelerating the snap block while simultaneously rotating the snap block.

7. The method as set forth in claim 5, further including:
    accelerating the snap block while simultaneously rotating the first carriage pickup element and a second carriage pickup element.

8. The method as set forth in claim 5, further including:
    withdrawing the subject support from the imaging region and decelerating the accessory carriage to rest using a second carriage pickup element.

9. The method as set forth in claim 8, wherein the step of decelerating the accessory carriage includes camming a pin against a second camming surface causing the snap block to rotate and a pin to enter a deceleration groove of the second carriage pickup element.

10. A pickup mechanism by which a linearly translating subject support picks up an accessory carriage so as to transfer the accessory carriage with the subject support into an imaging system, the pickup mechanism comprising:
    a first structure connected with the subject support; and
    a second structure connected with the accessory carriage; one of the first and second structures being a rotatable element, the first and second structures engaging together responsive to linear translation of the subject support into the imaging system, the rotatable element rotating during the engagement so as to gradually accelerate the accessory carriage up to the linear translation speed of the linearly translating subject support.

11. The pickup mechanism as set forth in claim 10, wherein the second structure is the rotatable element and is connected with the accessory carriage via a pivot pin.

12. The pickup mechanism as set forth in claim 11, wherein the first and second structures engage by camming to cause rotation of the rotatable element about the pivot pin, and the camming is along an acceleration groove having a curvature providing a selected acceleration profile for the accessory carriage.

13. The pickup mechanism as set forth in claim 10, further comprising:
    a third structure, one of the second and third structures being a rotatable element, the second and third structures engaging together responsive to linear translation of the subject support out of the imaging system, the rotatable element rotating during the engagement so as to gradually decelerate the accessory carriage from the linear translation speed of the linearly translating subject support to stationary.

14. The pickup mechanism as set forth in claim 13, wherein the first and third structures are mirror images of each other and the second structure is bilaterally symmetric.

15. A magnetic resonance system comprising:
    a magnetic resonance scanner;
    a couch or trolley;
    a subject support configured to linearly translate from the couch or trolley into the magnetic resonance scanner to load a subject into the scanner;
    an accessory carriage disposed to linearly translate from the couch or trolley into the magnetic resonance scanner to load into the scanner; and
    a pickup mechanism as set forth in claim 10 arranged to pick up the accessory carriage as the subject support linearly translates from the couch or trolley into the magnetic resonance scanner.

* * * * *